(12) United States Patent
Noble et al.

(10) Patent No.: US 12,653,677 B2
(45) Date of Patent: Jun. 16, 2026

(54) IMPLANT

(71) Applicants: Aaron Noble, Newnan, GA (US); Spencer Jones, Newnan, GA (US)

(72) Inventors: Aaron Noble, Newnan, GA (US); Spencer Jones, Newnan, GA (US)

(73) Assignee: Poriferous, LLC., Newnan, GA (US)

( * ) Notice: Subject to any disclaimer, the term of this patent is extended or adjusted under 35 U.S.C. 154(b) by 775 days.

(21) Appl. No.: 18/057,378

(22) Filed: Nov. 21, 2022

(65) Prior Publication Data

US 2023/0165682 A1 Jun. 1, 2023

Related U.S. Application Data

(60) Provisional application No. 63/283,346, filed on Nov. 26, 2021.

(51) Int. Cl.
A61F 2/28 (2006.01)
A61F 2/00 (2006.01)
(Continued)

(52) U.S. Cl.
CPC .......... A61F 2/2875 (2013.01); A61F 2/0063 (2013.01); A61F 2/28 (2013.01);
(Continued)

(58) Field of Classification Search
CPC .. A61F 2/2875; A61F 2/3872; A61F 2/30767; A61F 2002/30769;
(Continued)

(56) References Cited

U.S. PATENT DOCUMENTS 4,542,539 A * 9/1985 Rowe, Jr. .................. A61F 2/30
606/76
6,031,148 A * 2/2000 Hayes ................... A61F 2/0077
606/154
(Continued)

FOREIGN PATENT DOCUMENTS

CN 106859816 A * 6/2017 ............. B33Y 80/00
CN 108289733 A * 7/2018 ......... A61F 2/30756
(Continued)

OTHER PUBLICATIONS

International Patent Application No. PCT/US2022/080226, International Search Report and Written Opinion mailed Mar. 15, 2023, 13 pages.

*Primary Examiner* — Alvin J Stewart
(74) *Attorney, Agent, or Firm* — Kilpatrick Townsend & Stockton, LLP

(57) ABSTRACT

An implant may include a curved implant body and a flange extending from the implant body, the flange being thinner than the implant body, the implant body and the flange having a first exterior surface and a second exterior surface opposite the first surface in which the implant body and the flange formed by at least partially fused particles. The particles at the first surface define a first average pore size and the particles at the second surface define a second average pore size; with the first average pore size being greater than the second average pore size. The first surface may be a tissue ingrowth surface and the second surface may be a tissue ingrowth barrier.

20 Claims, 10 Drawing Sheets

(51) Int. Cl.
  *A61F 2/30*    (2006.01)
  *A61F 2/44*    (2006.01)
  *A61F 2/46*    (2006.01)
(52) U.S. Cl.
  CPC .............. *A61F 2/3094* (2013.01); *A61F 2/44*
    (2013.01); *A61F 2/4611* (2013.01)
(58) Field of Classification Search
  CPC .............. A61F 2/30724; A61F 2/30734; A61F
    2002/30736; A61F 2002/30751; A61F
    2002/30011; A61F 2002/2878; A61F
    2002/2882; A61F 2002/282885; A61F
    2002/2889; A61F 2002/30968
  See application file for complete search history.

(56)     References Cited

U.S. PATENT DOCUMENTS

| | | | | |
|---|---|---|---|---|
| 6,350,284 | B1 * | 2/2002 | Tormala | A61F 2/2846 |
| | | | | 623/16.11 |
| 6,852,330 | B2 * | 2/2005 | Bowman | A61L 27/44 |
| | | | | 428/116 |
| 8,287,915 | B2 * | 10/2012 | Clineff | A61L 27/46 |
| | | | | 424/602 |
| 8,398,720 | B2 * | 3/2013 | Swords | A61F 2/30965 |
| | | | | 623/23.72 |
| 10,945,845 | B2 * | 3/2021 | Ricci | A61L 27/54 |
| 11,013,602 | B2 * | 5/2021 | Bonutti | A61L 27/24 |
| 12,076,244 | B1 * | 9/2024 | Folsom | A61N 7/00 |
| 2002/0120348 | A1 * | 8/2002 | Melican | A61F 2/0045 |
| | | | | 623/23.72 |
| 2003/0004578 | A1 * | 1/2003 | Brown | A61L 27/46 |
| | | | | 623/23.72 |
| 2003/0042641 | A1 * | 3/2003 | Abe | B29C 64/165 |
| | | | | 264/112 |
| 2004/0138591 | A1 * | 7/2004 | Iseki | A61F 2/30942 |
| | | | | 600/587 |
| 2006/0224242 | A1 * | 10/2006 | Swords | A61B 17/8085 |
| | | | | 606/915 |
| 2007/0142914 | A1 * | 6/2007 | Jones | B23K 26/382 |
| | | | | 623/14.13 |
| 2009/0068245 | A1 * | 3/2009 | Noble | A61L 27/446 |
| | | | | 521/142 |
| 2009/0157182 | A1 * | 6/2009 | Koblish | A61F 2/28 |
| | | | | 623/23.72 |
| 2009/0292367 | A1 * | 11/2009 | Borden | A61F 2/28 |
| | | | | 427/2.24 |
| 2010/0023130 | A1 | 1/2010 | Henry et al. | |
| 2010/0137990 | A1 * | 6/2010 | Apatsidis | A61F 2/4425 |
| | | | | 606/301 |
| 2010/0331979 | A1 * | 12/2010 | McDade | A61L 27/52 |
| | | | | 623/14.12 |
| 2013/0178947 | A1 * | 7/2013 | Monaghan | A61L 27/04 |
| | | | | 623/23.55 |
| 2013/0231754 | A1 * | 9/2013 | Daigo | B22F 3/1125 |
| | | | | 623/23.55 |
| 2015/0150681 | A1 * | 6/2015 | Ricci | A61F 2/2875 |
| | | | | 264/340 |
| 2016/0038289 | A1 * | 2/2016 | Noble | A61F 2/2875 |
| | | | | 264/41 |
| 2017/0281350 | A1 * | 10/2017 | Noble | A61F 2/2875 |
| 2018/0200064 | A1 * | 7/2018 | Vallittu | A61F 2/2875 |
| 2020/0030102 | A1 * | 1/2020 | Mullens | A61F 2/34 |
| 2020/0197180 | A1 * | 6/2020 | Christopher | A61B 5/0059 |
| 2022/0061993 | A1 * | 3/2022 | Shim | A61B 34/10 |
| 2022/0168104 | A1 * | 6/2022 | Aksu | A61F 2/30771 |
| 2022/0202574 | A1 * | 6/2022 | Kuhn | A61L 31/086 |
| 2022/0202575 | A1 * | 6/2022 | Noble | A61B 17/86 |
| 2023/0225870 | A1 * | 7/2023 | Yao | A61C 8/00 |
| | | | | 623/20.32 |
| 2024/0148508 | A1 * | 5/2024 | Aksu | A61F 2/30734 |
| 2024/0277478 | A1 * | 8/2024 | Sirichatchai | A61F 2/2803 |
| 2025/0025304 | A1 * | 1/2025 | Mai | A61F 2/4225 |
| 2025/0114203 | A1 * | 4/2025 | Hunt | A61F 2/2875 |

FOREIGN PATENT DOCUMENTS

| | | | | | |
|---|---|---|---|---|---|
| CN | 112641538 | A | * | 4/2021 | A61F 2/2875 |
| CN | 114404113 | A | * | 4/2022 | A61L 27/50 |
| DE | 102021201695 | A1 | * | 8/2022 | A61F 2/2846 |
| DE | 102022110936 | A1 | * | 6/2023 | C23C 4/08 |
| KR | 102313998 | B1 | * | 10/2021 | A61L 27/56 |
| WO | WO-2025038862 | A1 | * | 2/2025 | A61F 2/3859 |

* cited by examiner

114

116

126
124
122
120
118

IMPLANT

CROSS REFERENCE TO RELATED APPLICATIONS

This application claims priority to, and the benefit of the filing date of, U.S. Provisional Patent Application Ser. No. 63/283,346 filed Nov. 26, 2021, the entire contents of which is incorporated by reference.

RELATED FIELDS

Implants, such as craniofacial implants, that are formed by fusing or at least partially fusing particles.

BACKGROUND

Implants, such as craniofacial implants, that are formed by fusing or at least partially fusing particles are known in the prior art, however, there remains room for improvement in this art. This patent describes improved implants, including improved craniofacial implants.

SUMMARY

This patent describes improved implants, including improved craniofacial implants with implant bodies that have been formed by at least partially fused particles formed in a manner such that the implant has a variable average pore size across its thickness, with one surface of the implant having a larger average pore size than pores on the opposite side. Such an implant may present several advantages over prior art implants, including prior art sintered implants. For example, in some implementations, varying average pore size between the surfaces may functionalize the implant such that one surface is optimized for promoting tissue ingrowth while the other surface resists tissue ingrowth. In these and other implementations, varying average pore size enhance the implant's mechanical properties, allowing for stronger, thinner sintered implants than have been achieved in the past.

In one example, an implant includes an implant body formed by numerous at least partially fused particles, the implant body having a first exterior surface and a second exterior surface opposite the first surface; the particles at the first surface define a first average pore size and the particles at the second surface define a second average pore size; and the first average pore size is greater than the second average pore size.

In this example, the implant may be a craniofacial implant.

In this example, the first surface may be a tissue ingrowth surface and the second surface may be a dura facing surface.

In this example, the dura facing surface may be a barrier to tissue ingrowth.

In this example, both the first and second surfaces may be at least partially curved.

In this example, the implant may further include a flange extending from the implant body and formed by the at least partially fused particles, the flange having a first flange surface and a second flange surface opposite the first surface; the particles at the first flange surface defining a first average flange pore size and the particles at the second flange surface defining a second average flange pore size; and the first average flange pore size being greater than the second average flange pore size.

In this example, the flange thickness (the thickness between the first and second flange surfaces) may be less than 1 mm.

In this example, the implant body may be thicker than the flange.

In this example, the flange may be configured to receive and retain fasteners.

In this example, the implant may define a porosity gradient between the first and second surfaces.

In this example, the first average pore size may be at least 100 μm greater than the second average pore size.

In this example, an average pore size at a mid-level between the first and second surfaces may be less than the first average pore size at the first surface and greater than the second average pore size at the second surface.

In another example, an implant includes: a curved implant body and a flange extending from the implant body, the flange being thinner than the implant body, the implant body and the flange having a first exterior surface and a second exterior surface opposite the first surface; the implant body and the flange formed by at least partially fused particles; the particles at the first surface defining a first average pore size and the particles at the second surface defining a second average pore size; the first average pore size being greater than the second average pore size; the first surface being a tissue ingrowth surface and the second surface being a tissue ingrowth barrier.

In this example, the implant may be a craniofacial implant.

In this example, the flange may be configured to receive and retain fasteners, the flange thickness being less than 1 mm.

In this example, the implant may define a porosity gradient between the first and second surfaces.

In this example, the first average pore size may be at least 50 μm greater than the second average pore size.

In this example, the first average pore size may be at least 100 μm greater than the second average pore size.

In this example, the first average pore size may be at least 200 μm greater than the second average pore size.

In this example, an average pore size at a mid-level between the first and second surfaces may be less than the first average pore size at the first surface and greater than the second average pore size at the second surface.

In this example, the porosity gradient may include different average pore sizes at a first, second, and third levels between the first and second surfaces, in which the first level is between the first surface and the second level, the second level is between the first and third levels, and the third level is between the second level and the second surface, in which: (i) an average pore size at the first level may be less than the first average pore size at the first surface and greater than an average pore size at the second level; (ii) the average pore size at the second level may be less than the average pore size at the first level and greater than an average pore size at the third level; (iii) the average pore size at the third level may be less than the average pore size at the second level and greater than the second average pore size at the second level.

In another example, a method of making an implant may include positioning particles between a first heated mold surface and a second heated mold surface; applying heat and compression to at least partially fuse the particles and form the implant such that the implant has: (i) an implant body formed by the plurality of at least partially fused particles, the implant body having a first exterior surface corresponding in geometry to the first heated mold surface and a second exterior surface corresponding in geometry to the second heated mold surface, the second exterior surface opposite the first exterior surface; (ii) the particles at the first exterior surface defining a first average pore size and the particles at the second exterior surface defining a second average pore size; the first average pore size being greater than the second average pore size.

In this example, the second heated mold surface may be heated to a higher temperature than the first heated mold surface.

In this example, the first and second heated mold surfaces may be curved surfaces.

In this example, the first exterior surface of the formed implant may be a tissue ingrowth surface and the second exterior surface of the formed implant may be a barrier to tissue ingrowth.

In this example, the formed implant may define a porosity gradient between the first and second surfaces.

In this example, the first average pore size may be at least 50 μm greater than the second average pore size.

In this example, the first average pore size may be at least 100 μm greater than the second average pore size.

In this example, the first average pore size is at least 200 μm greater than the second average pore size.

DETAILED DESCRIPTION

Figure 1:
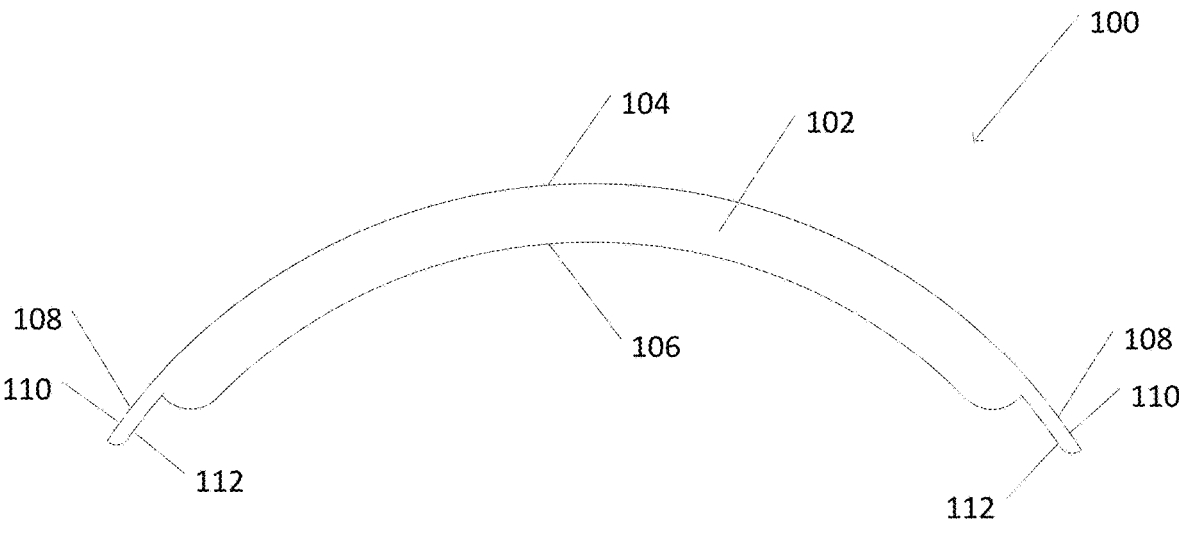
FIG. 1 shows an example of an implant.

FIG. 1 shows an example of an implant 100. In this example, implant 100 is a sintered implant formed by applying heat and pressure to individual particles or fines (e.g. polyethylene or other plastic particles or fines) to fuse or at least partially fuse the particles or fines into a coherent mass. The implant 100 of FIG. 1 includes an implant body 102 having a first exterior surface 104 and a second exterior surface 106 opposite the first exterior surface 104.

The sintered implant 100 defines a porosity gradient between the first exterior surface 104 and the second interior surface 106. In this particular example, the particles at the first exterior surface 104 define an average pore size that is greater than the average pore size defined by the particles at the second exterior surface 106. In some implementations, the average pore size at the first exterior surface 104 may be at least 50 μm greater than the average pore size at the second exterior surface 106. In some implementations, the average pore size at the first exterior surface 104 may be at least 100 μm greater than the average pore size at the second exterior surface 106. In some implementations, the average pore size at the first exterior surface 104 may be at least 200 μm greater than the average pore size at the second exterior surface 106.

In some implementations, for implantation, the more porous layer faces away from the patient's bone and the less porous layer abuts the bone to be re-grown or repaired.

In the example of FIG. 1, the first exterior surface 104 with the greater average pore size is configured to promote tissue ingrowth whereas the second exterior surface 106 with the lesser average pore size is configured to resist or act as barrier to tissue ingrowth. For instance, in the particular example shown in FIG. 1, the implant 100 is a craniofacial implant in which the first exterior surface 104 is configured to promote tissue ingrowth and the second exterior surface 106 is a dura-facing surface configured to resist or act as a barrier to tissue ingrowth, to avoid or lessen the chance of damage to the dura should the implant need to be removed or revised.

As noted above, the implant 100 in the example of FIG. 1 is a craniofacial implant. Implant body 102 is curved with the first and second exterior surfaces 104, 106 curved and otherwise shaped and size for the specific procedure that the implant 100 will be used for. In some instances, the implant 100 may be custom manufactured to a patient's specific anatomy. In some instances, the sintered material of implant 100 may be trimmable for in situ customization of the implant to a patient's specific anatomy.

The implant 100 shown in FIG. 1 includes a flange 108 that may extend completely or partially around the implant body 102. In this example, flange 108 is thinner and configured to overlie adjacent bony anatomy of the patient. The inventors have discovered that due to the novel porosity gradient of the implant 100, the flange 108 may unexpectedly be made of a relatively thin flange thickness while still being configured to receive and retain fasteners (e.g. bone screws or other orthopaedic fasteners) without implant breakage or other failure. In some implementations, the thickness of the flange 108 may be less than 1 mm.

Flange 108 may be formed in the same sintering process and of the same material as the implant body 102. The flange 108 in FIG. 1 includes a first flange surface 110 adjacent the first exterior surface 104 of the implant body 102 and a second flange surface 112 adjacent the second exterior surface 106 of the implant body 102. The first flange surface 110 is opposite the second flange surface 112. As with the first and second exterior surfaces 104, 106 of the implant body 102, the first flange surface 110 defines an average pore size that is greater than the average pore size at the second flange surface 112. In some implementations, the average pore size at the first flange surface 110 may be substantially the same as the average pore size at the first exterior surface 104 of the implant body 102, and the average pore size at the second flange surface 112 may be substantially the same as the average pore size at the second exterior surface 106 of the implant body 102. In other implantations, the average pore size at the first flange surface 110 is not the same as the average pore size at the first exterior surface 104, and the average pore size at the second flange surface 112 is note the same as the average pore size at the second exterior surface 106.

In some implementations, the implant is an integral implant that is formed via differentially heated plates that form the varied porosity of the two sides. The implant may be a one-piece implant that is formed of the same base material throughout. In other words, it is not formed by the typical prior art methods of laminating or otherwise adhering two layers of materials that have differing porosities to one another (e.g., a porous layer and a non-porous layer) to form surfaces of differing porosities. Instead, the implant may be formed using a mold that has upper and lower compression plates (e.g. plates 114, 116 in FIG. 2) of varying temperatures. In other implementations, the implant may be formed in other methods.

Figure 2:
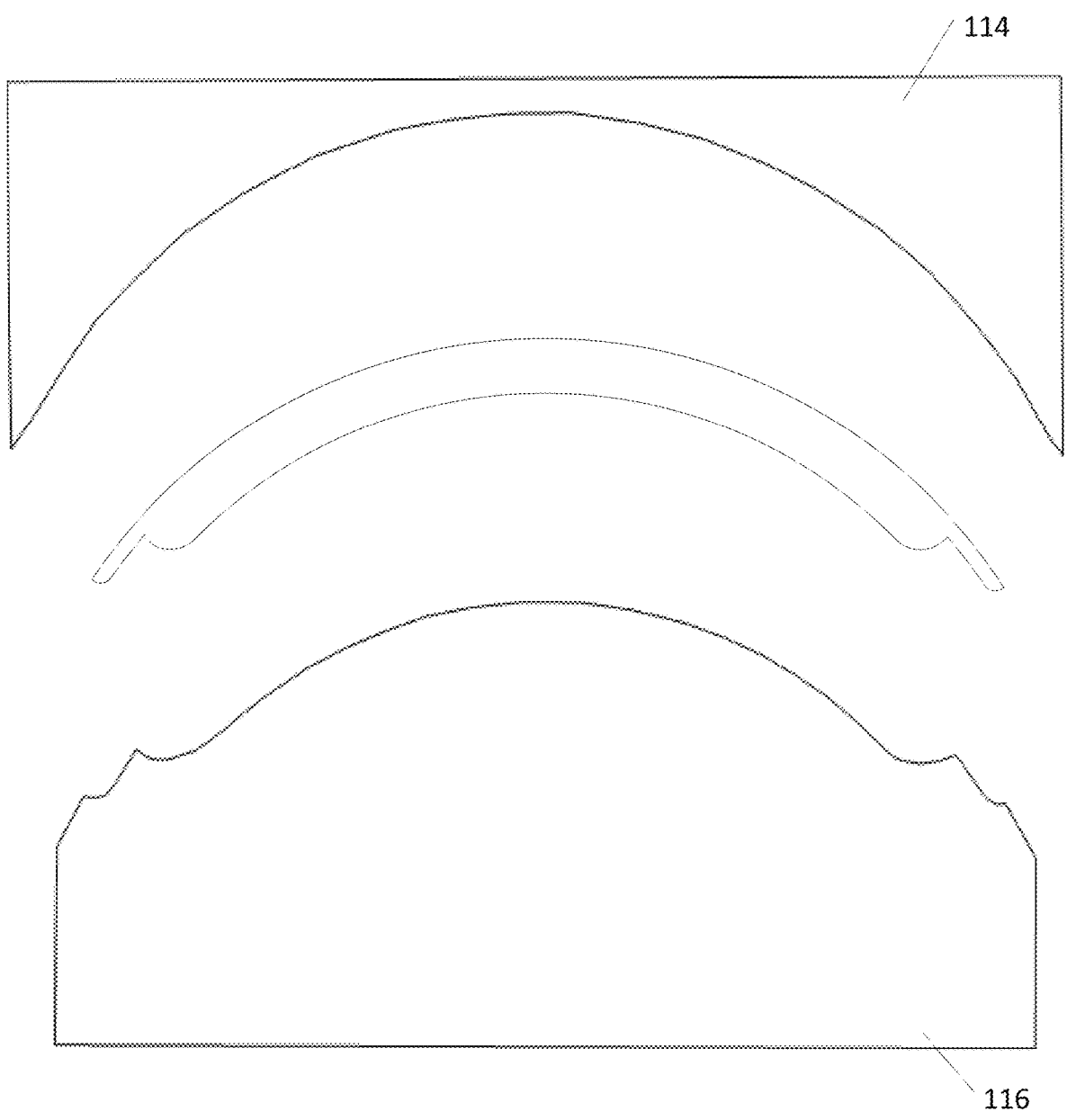
FIG. 2 shows the implant of FIG. 1 along with an example of a mold for making the implant.

In the example shown in FIG. 2, the compression plates 114, 116 are generally provided having two different temperatures, such that one plate has a lower heat or temperature than a second plate. During manufacture, the material used to form the implant is put into the mold. This material used is typically particles (or fines) of polyethylene or a polyethylene mixture or other appropriate implant material that can be formed into an implant via heat and compression. Other materials or combinations of materials may be used and are considered within the scope of this disclosure. The plates of differing temperatures are then pressed against the material to form the implant. The process may be referred to as "sintering" because the particles do not fully melt and fuse to one another all the way through the implant. Instead, some particles at the surface of the higher temperature plate may soften and "stick" or otherwise adhere to one another, but the particles do not melt to the point of fusion.

The above described manufacturing method or other manufacturing methods may be employed to achieve a gradient of porosity throughout the implant. For example, rather than having a clear division between porosities or layers, which is what would occur when two separate layers of material are laminated or otherwise adhered to one another, the implant is made of the same materials throughout, such that as porosity changes between the first surface, through the implant, to the second surface, there may be a porosity gradient that slowly changes from more to less porous (or vice versa, depending upon which surface is considered the starting point for testing).

Figure 3:
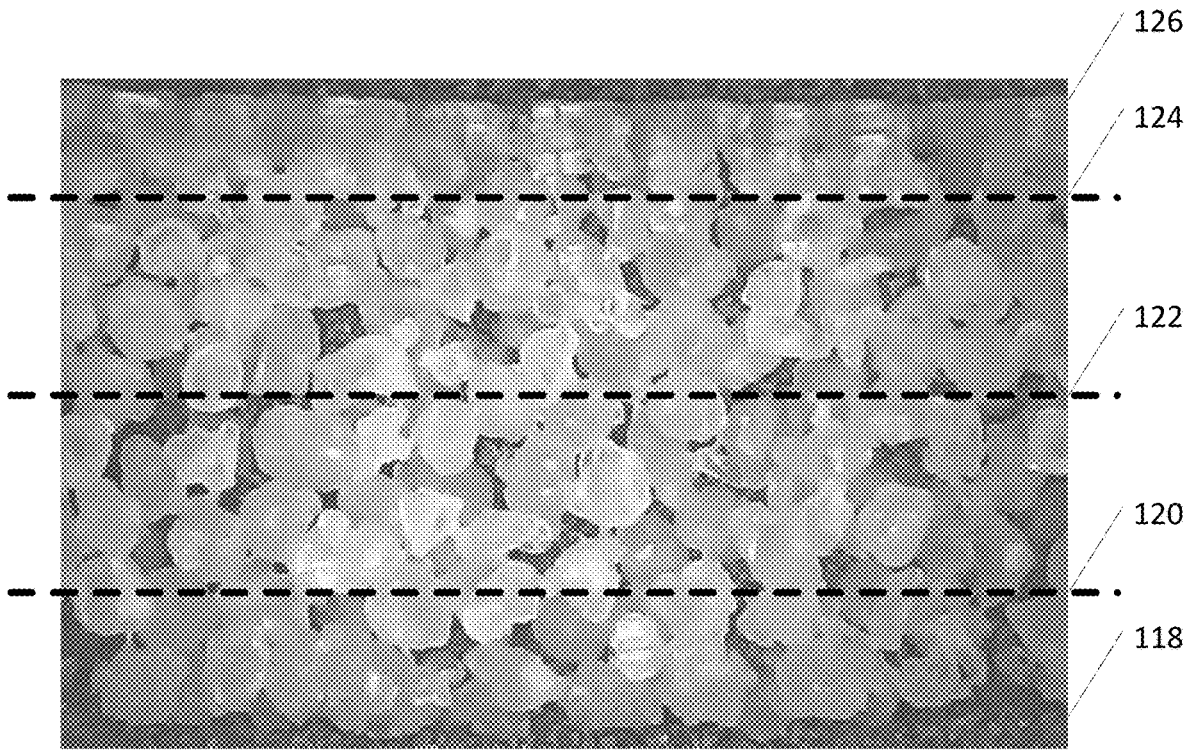
FIG. 3 shows a cross-section of an implant defining a porosity gradient between its exterior surfaces.

For example, FIG. 3 shows a cross-section of a sintered implant with a gradient of porosity throughout the implant between a first exterior surface 118 and a second exterior surface 126. In the example of FIG. 3, the average pore size at the first exterior surface 118 is greater than the average pore size at the second exterior surface 126 and there is a gradient of porosity between the first and second exterior surfaces 118, 126. The average pore size at level 120 is lower than the average pore size at the first exterior surface 118. The average pore size at level 122 is lower than the average pore size at level 120. The average pore size at level 124 is lower than at level 122. The average pore size at the second exterior surface 126 is lower than at level 124.

Returning to the example of FIG. 2, the lower heat of the first plate 116 results in a more porous surface resulting on the exterior surface 104 of the implant 100 that is formed by the first plate 116. The higher heat of the second plate 114 results in a less porous (or perhaps even a solid or otherwise non-porous) exterior surface 106 on the side of the implant 100 that is formed by the second plate 114. The additional heat provided by the second plate 114 causes the particles of material on the second side/second surface 106 to sinter more fully to one another than does the lower heat of the first plate 116. This results in an integral implant having surfaces of varying porosities.

For example, in some implementations, the porosity at the surface of the non-porous side (the side that is formed by the hotter plate) may be between about 0 μm-80 μm. The porosity at the surface of the porous side (the side formed by the plate that is not as hot) may be between about 100 μm-1300 μm.

In some implementations, the temperature range of the first plate may be between about 80° F.-280° F. The temperature range of the first plate may result in a porosity range along various portions of the first surface of about 0 μm-80 μm. The temperature range of the second plate may be between about 280° F.-400 d° F. The temperature range of the second plate may result in a porosity range along various portions of the second surface of about 100 μm-1300 μm.

It should be understood that these ranges are provided for exemplary reasons and that other ranges are possible and considered within the scope of this disclosure. It should also be understood that the manufacturing method schematically illustrated in FIG. 2 is provided for exemplary reasons only and that other manufacturing methods could be employed to manufacture a sintered implant having a porosity gradient between a first and second surface.

Returning to FIG. 2, the form of the mold including the upper and lower mold plates 114, 166, may result in the formation of a flange 108 around the perimeter of the implant. The flange may be used for implantation purposes. For example, the flange may receive a fixation structure used to secure the implant to patient bone. In some implementations, the flange may be fully solid/porous surface. In some implementations, the flange may include a less porous surface and a more porous surface opposite the less porous surface, corresponding to the less and more porous surfaces of the implant's main body.

Figure 4:
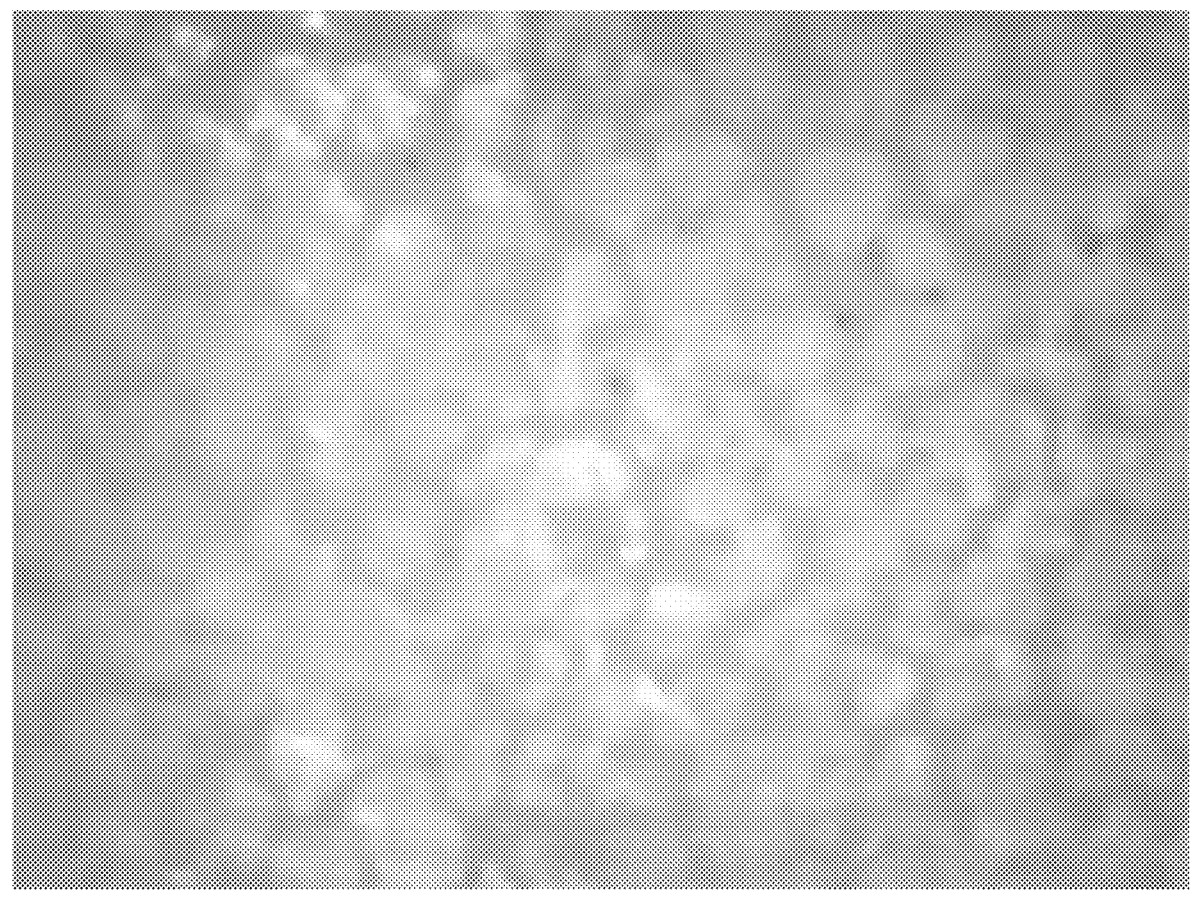
FIG. 4 shows an exterior surface of the implant of FIG. 3.
Figure 5:
FIG. 5 shows the opposite exterior surface of the implant of FIG. 3.

FIGS. 3-5 show micrographs of an example implant. FIG. 3 shows a cross-sectional view, illustrating the particles that are sintered to one another but that retain a porosity throughout the body of the implant and at the surface 104. The upper surface 106 shows an area of particles that creates a relatively smooth and non-porous surface. The bottom surface 104 shows that pores remain present, even though application of heat and pressure still causes the particles to sinter and bind to one another. FIG. 4 shows upper surface 106 and FIG. 5 shows bottom surface 104.

Experimental Characterization of Pore Size

Figure 6:
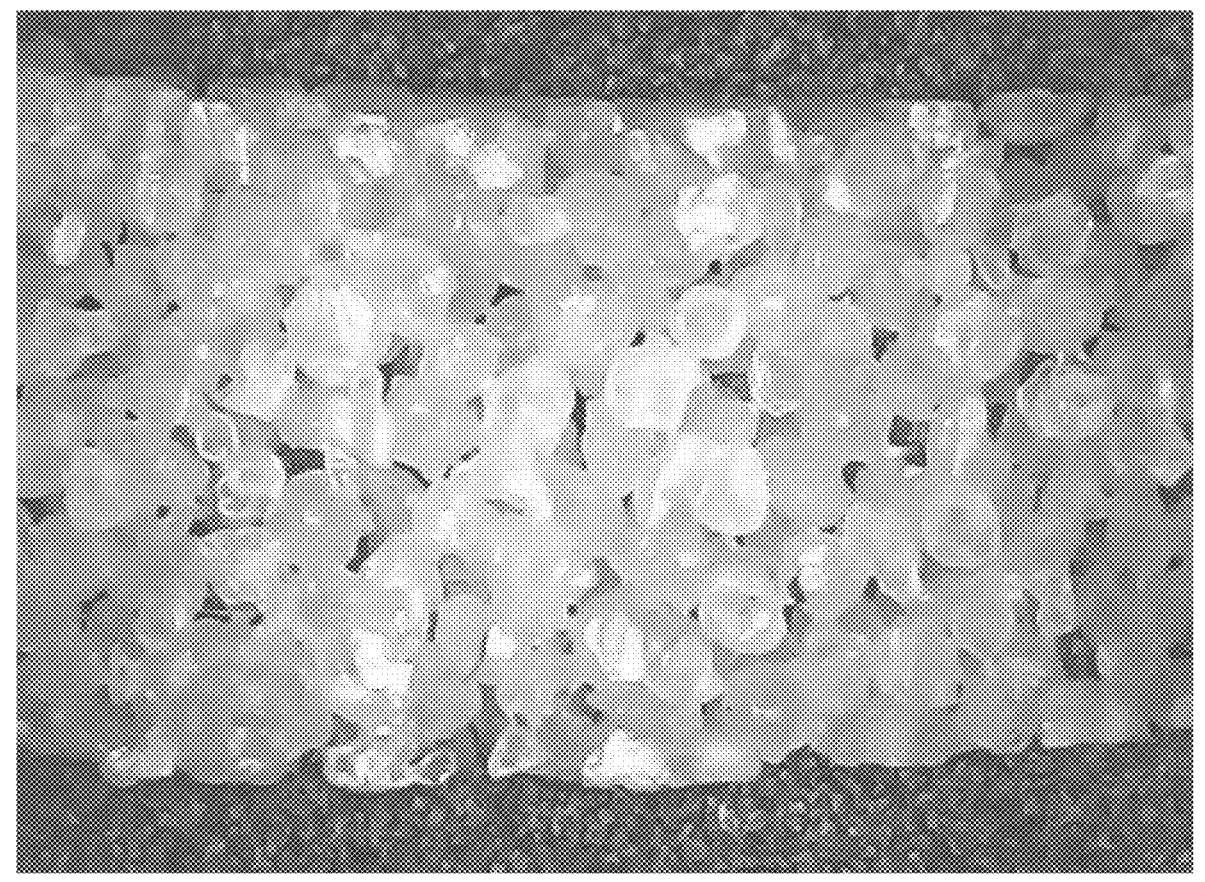
FIG. 6 shows a cross-section of an implant having a uniform porosity between its exterior surfaces.
Figure 7:
FIG. 7 shows an exterior surface of the implant of FIG. 6.
Figure 8:
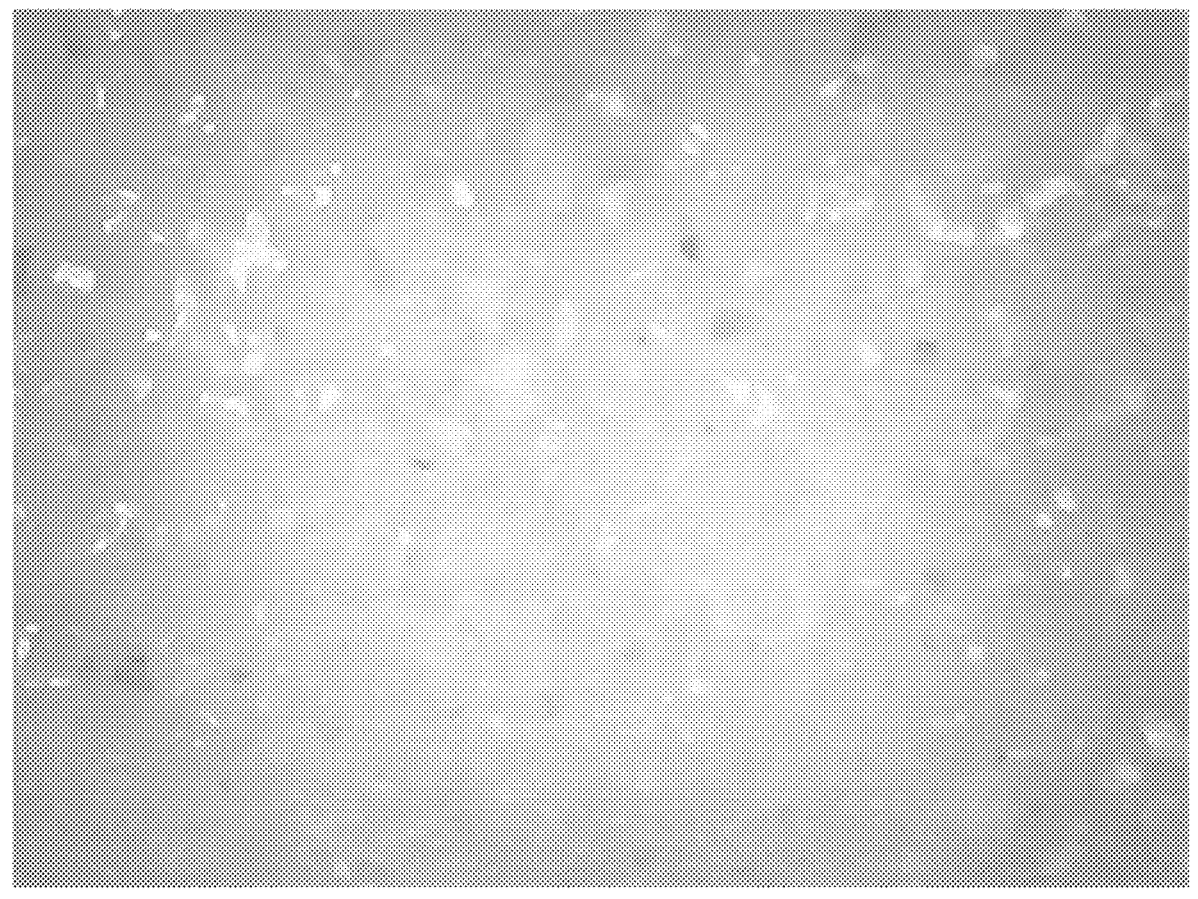
FIG. 8 shows the opposite exterior surface of the implant of FIG. 6.

In an experiment, average pore size was compared between a proposed design and a sample design. Additionally, two surfaces of the proposed design are compared against another to determine if there is any significant difference in average pore size. For the experiment, the "proposed" design had a bottom, porous surface and a top, smooth surface. A cross-sectional image of the proposed design is at FIG. 3, with FIGS. 4 and 5 showing the bottom and top surfaces respectively. For the experiment, the "sample" product is a product with a relatively uniform pore size throughout the entire product. A cross-sectional image of the sample product is at FIG. 6, with the bottom and top surfaces respectively shown at FIGS. 7 and 8.

In the first part of this experiment, the pore density (pore size) of the proposed designed was compared to the pore density (pore size) of the sample product. To conduct this experiment, a small section was cut off of each product to create samples of the products. These samples were cut further into thin slices, four from each sample, they were then used to measure the pore density of each sample. The pore density was calculated using a microscope and the AmScope software program. The software program was calibrated to one millimeter, and then the measuring tool in the program was used to measure the pore size of approximately thirty pores in two spots on each of the four slices from both samples. This data was used to find and compare the normal distribution curves for proposed design and sample.

In the second part of this experiment, the porous side (top side) of the proposed design was compared to the smooth side (bottom side) of the proposed design. The images of the proposed design that were used in part one of this experiment were also used in this part. Using the same methods as in part one, the bottom side (approximately one-third of each cross-sectional image) was measured with twenty measurements per image. While the top side (approximately two-thirds of each cross-sectional image) was measured with thirty measurements per image. The data created in this part was also used to find and compare the normal distribution curves of top and bottom surfaces.

Results and Discussion

Figure 9:
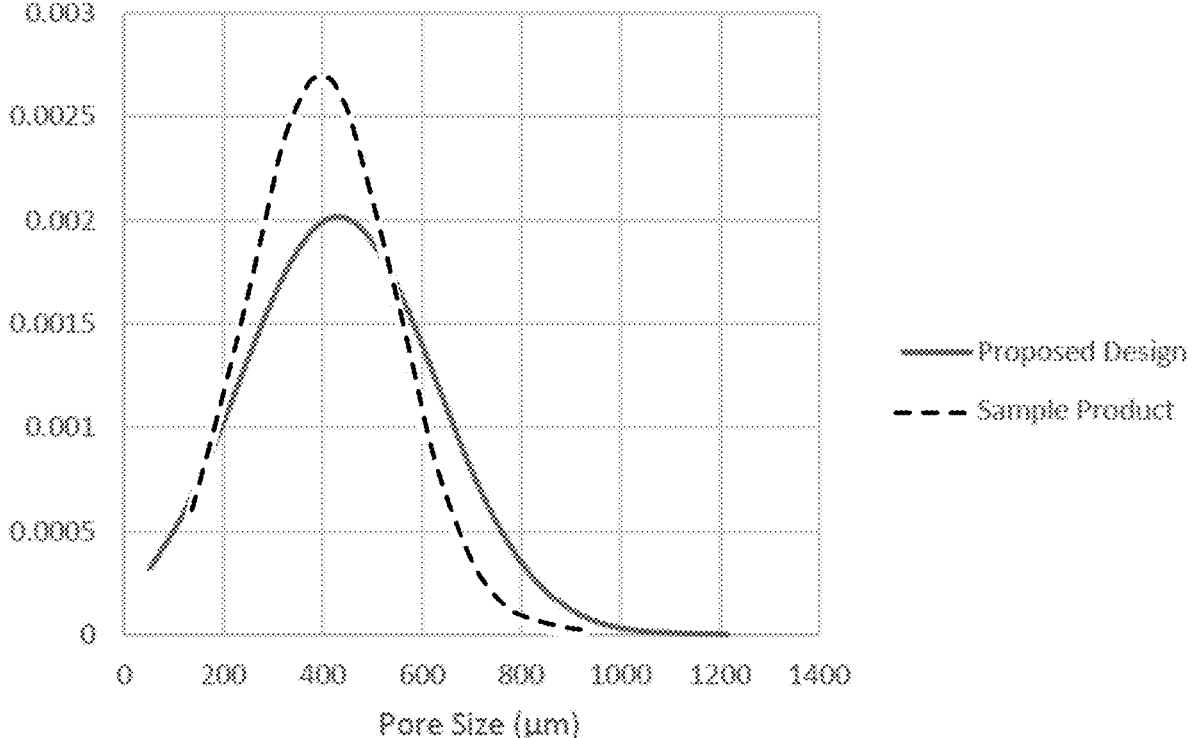
FIG. 9 shows a comparison of the pore size ranges of the implant of FIGS. 3-5 (the "Proposed Design" in FIG. 9) and the implant of FIGS. 6-8 (the "Sample Product" in FIG. 9).

The first part of this experiment found that the proposed design with pore size range of 1,164.13 μm, while the sample product only had a range of 791.04 μm. The ranges for each can be seen in table one and FIG. 9. From FIG. 9, it can also be determined that any given pore from the sample product has a higher probability of falling into this tight pore range. Table one shows the minimum, maximum, average, and standard deviations calculated from each data set. This data was used to find the normal distributions for each data set. The normal distribution curves for each data set can be seen in FIG. 9. All data is presented in micrometers (μm).

TABLE 1

|  | Proposed Design | Sample Product |
|---|---|---|
| Minimum (μm) | 51.12 | 132.58 |
| Maximum (μm) | 1215.25 | 923.62 |
| Average (μm) | 430.66 | 394.30 |
| Standard Deviation (μm) | 197.76 | 150.70 |

Figure 10:
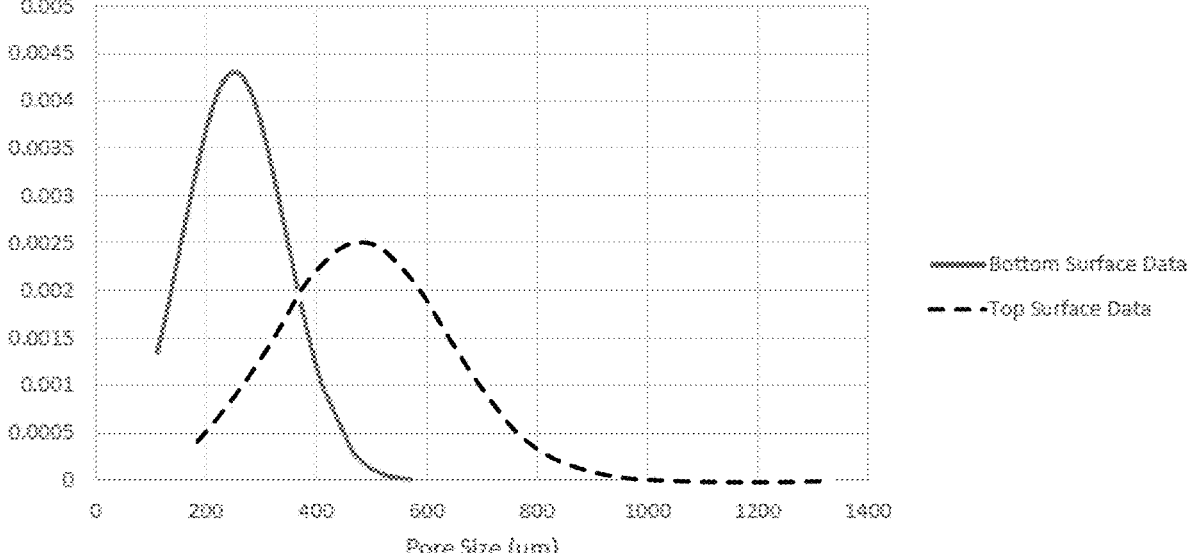
FIG. 10 shows a comparison of the pore sizes of the bottom (FIG. 4) and top (FIG. 5) exterior surfaces of the implant of FIGS. 3-5.

The second part of the experiment determined that the pores on the bottom surface of the proposed design were more densely packed than the pores on the top surface of the proposed design. The range of pores on the bottom surface is only 460.89 μm compared to the top surface's range at 1,141.83 μm. In addition, the probability of the pore size on the bottom surface being smaller than the pore sizes on the top surface is much higher. Table two and FIG. 10 below further displays this information.

Tab two shows the minimum, maximum, average, and standard deviations calculated from the proposed design's bottom and top surfaces. These data were used to calculate the normal distribution curves for each data set, that can be seen in figure two. All data is presented in micrometers (μm).

TABLE 2

|  | Bottom Surface Data | Top Surface Data |
|---|---|---|
| Minimum (μm) | 110.14 | 189.85 |
| Maximum (μm) | 571.03 | 1331.68 |
| Average (μm) | 251.69 | 484.17 |
| Standard Deviation (μm) | 92.67 | 158.51 |

Considering all the data and information presented in this report, it can be established that the proposed design has a more assorted variety of pore sizes and density when compared to the sample product. Moreover, the top surface of the proposed design is more porous than that of the bottom surface of the prosed design.

Experimental Characterization of Tensile Strength and Pull Out Resistance

In another experiment, we examined tensile strength, screw pull-out strength, and suture pull-out strength. In this experiment, a first group of specimens (the "Prior Art Specimens") were formed using prior art sintering techniques to sinter polyethylene fines into implant specimens with relatively uniform porosities. The Prior Art Specimens all had a thickness ranging from 1.33 mm to 1.43 mm. A second group of specimens (the "Variable Porosity Specimens") were formed using techniques in accordance with the present invention to sinter polyethylene fines into implant specimens with variable porosities as described above. The Variable Porosity Specimens all had a thickness ranging from 0.92 mm to 1.00 mm.

The following tables show the results of our testing, showing that the Variable Porosity Specimens have unexpectedly high tensile strength and resistance to screw and suture pull out compared to the Prior Art Specimens. The results are particularly unexpected given that the Variable Porosity Specimens are significantly thinner than the Prior Art Specimens.

TABLE 3

| Tensile Strength (Lbs.) Data | | |
|---|---|---|
| Specimen # | Prior Art Specimens | Variable Porosity Specimens |
| 1 | 6.25 | 17.3 |
| 2 | 8 | 19.81 |
| 3 | 9.56 | 20.5 |
| 4 | 8.31 | 15.62 |
| 5 | 10.75 | 16.25 |
| 6 | 7.5 | 14.125 |
| 7 | 10.18 | 14.68 |
| 8 | 10.56 | 17.18 |
| 9 | 10.5 | 16.5 |
| 10 | 7.87 | 15.12 |
| Standard Deviation | 1.563136448 | 2.090138286 |

TABLE 4

| Screw Pull-Out Strength (Lbs.) Data | | |
|---|---|---|
| Specimen # | Prior Art Specimens | Variable Porosity Specimens |
| 1 | 3.67 | 7.44 |
| 2 | 2.48 | 8.06 |
| 3 | 4.03 | 8.05 |
| 4 | 4.98 | 7.12 |
| 5 | 4.65 | 7.72 |
| 6 | 5.55 | 8.18 |
| 7 | 3.75 | 7.4 |
| 8 | 3.68 | 8 |
| 9 | 4.36 | 8.3 |
| 10 | 4.05 | 8.3 |
| Standard Deviation | 0.840542153 | 0.413710849 |

TABLE 5

| Suture Pull-Out Strength (Lbs.) Data | | |
|---|---|---|
| Specimen # | Prior Art Specimens | Variable Porosity Specimens |
| 1 | 7.2 | 10.48 |
| 2 | 6.4 | 12.25 |
| 3 | 6.74 | 9.18 |

TABLE 5-continued

| Suture Pull-Out Strength (Lbs.) Data | | |
| --- | --- | --- |
| Specimen # | Prior Art Specimens | Variable Porosity Specimens |
| 4 | 6.59 | 11.43 |
| 5 | 4.83 | 12.56 |
| 6 | 5.22 | 10.5 |
| 7 | 6.45 | 11.68 |
| 8 | 6.19 | 12.12 |
| 9 | 7.93 | 11 |
| 10 | 7.11 | 12.37 |
| Standard Deviation | 0.912690772 | 1.071499987 |

Accordingly, the Variable Porosity Specimens allow for implants with much thinner flange profiles while maintaining acceptable and even improved performance over the prior art. Thinner flange profiles are desirable in many instances because they allow for much smoother transitions between the implant and the patient's native anatomy.

Examples of the present invention have been described herein, including the best mode known to the inventors for carrying out the invention. The invention is susceptible to various modifications and alternative constructions, and exemplary embodiments have been shown and described in detail. Variations of those embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claim appended hereto as permitted by applicable law. Moreover, any combination of the above-described elements in all possible variations thereof is encompassed by the invention unless otherwise indicted herein or otherwise clearly contradicted by context.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclose. It will be apparent to one of ordinary skill in the art that many modifications and variations are possible in view of the above teachings.

We claim:

1. An implant, comprising:
a curved implant body and a flange extending from the implant body, the flange being thinner than the implant body, the implant body and the flange having a first exterior surface and a second exterior surface opposite the first surface, and the flange having a first flange surface and a second flange surface opposite the first flange surface, wherein;
the implant body and the flange formed by at least partially fused particles;
the particles at the first surface define a first average pore size and the particles at the second surface define a second average pore size, the first average pore size is greater than the second average pore size, and the first surface is a tissue ingrowth surface and the second surface is a tissue ingrowth barrier; and
the particles at the first flange surface define a first average flange pore size and the particles at the second flange surface define a second average flange pore size, and the first average flange pore size is greater than the second average flange pore size.

2. The implant of claim 1, wherein the implant is a craniofacial implant.

3. The implant of claim 1, wherein the flange is configured to receive and retain fasteners, wherein the flange thickness is less than 1 mm.

4. The implant of claim 1, wherein the implant defines a porosity gradient between the first and second surfaces.

5. The implant of claim 4, wherein the first average pore size is at least 50 μm greater than the second average pore size.

6. The implant of claim 4, wherein the first average pore size is at least 100 μm greater than the second average pore size.

7. The implant of claim 4, wherein the first average pore size is at least 200 μm greater than the second average pore size.

8. The implant of claim 4, wherein an average pore size at a mid-level between the first and second surfaces is less than the first average pore size at the first surface and greater than the second average pore size at the second surface.

9. The implant of claim 4, wherein the porosity gradient includes different average pore sizes at a first, second, and third levels between the first and second surfaces, in which the first level is between the first surface and the second level, the second level is between the first and third levels, and the third level is between the second level and the second surface, wherein:
  (i) an average pore size at the first level is less than the first average pore size at the first surface and greater than an average pore size at the second level;
  (ii) the average pore size at the second level is less than the average pore size at the first level and greater than an average pore size at the third level;
  (iii) the average pore size at the third level is less than the average pore size at the second level and greater than the second average pore size at the second surface.

10. An implant, comprising:
an implant body formed by a plurality of at least partially fused particles, the implant body having a first exterior surface and a second exterior surface opposite the first surface, wherein:
  the particles at the first surface define a first average pore size and the particles at the second surface define a second average pore size; and
  the first average pore size is greater than the second average pore size; and
a flange extending from the implant body and formed by the at least partially fused particles, the flange having a first flange surface and a second flange surface opposite the first surface, wherein:
  the particles at the first flange surface define a first average flange pore size and the particles at the second flange surface define a second average flange pore size; and
  the first average flange pore size is greater than the second average flange pore size.

11. The implant of claim 10, wherein the implant is a craniofacial implant.

12. The implant of claim 11, wherein the first surface is a tissue ingrowth surface and wherein the second surface is a dura facing surface.

13. The implant of claim 12, wherein the dura facing surface is a barrier to tissue ingrowth.

14. The implant of claim 12, wherein the first and second surfaces are both at least partially curved.

15. The implant of claim 10, wherein the flange comprises a flange thickness between the first and second flange surfaces, wherein the flange thickness is less than 1 mm.

16. The implant of claim 10, wherein the implant body is thicker than the flange.

17. The implant of claim 10, wherein the flange is configured to receive and retain fasteners.

18. The implant of claim 10, wherein the implant defines a porosity gradient between the first and second surfaces.

19. The implant of claim 18, wherein the first average pore size is at least 100 $\mu$m greater than the second average pore size.

20. The implant of claim 18, wherein an average pore size at a mid-level between the first and second surfaces is less than the first average pore size at the first surface and greater than the second average pore size at the second surface.

\* \* \* \* \*